United States Patent [19]

Azuma et al.

[11] Patent Number: 4,479,145
[45] Date of Patent: Oct. 23, 1984

[54] APPARATUS FOR DETECTING THE DEFECT OF PATTERN

[75] Inventors: Toru Azuma, Tokyo; Junji Hazama, Kawasaki; Atsushi Kawahara, Kawasaki; Kazunari Hada, Kawasaki; Norio Fujii, Urawa, all of Japan

[73] Assignee: Nippon Kogaku K.K., Tokyo, Japan

[21] Appl. No.: 400,681

[22] Filed: Jul. 22, 1982

[30] Foreign Application Priority Data

Jul. 29, 1981 [JP] Japan ............................ 56-117816
Jul. 29, 1981 [JP] Japan ............................ 56-117817
Jul. 29, 1981 [JP] Japan ............................ 56-117818
Jul. 29, 1981 [JP] Japan ............................ 56-117819
Jul. 29, 1981 [JP] Japan ............................ 56-117820

[51] Int. Cl.³ ............................................ H04N 7/18
[52] U.S. Cl. .................................. 358/106; 358/101; 358/107; 382/8; 382/48
[58] Field of Search ...................... 358/106, 107, 101; 382/8, 48

[56] References Cited

U.S. PATENT DOCUMENTS 4,238,780 12/1980 Doemens ............................ 382/8
4,364,086 12/1982 Guth .................................. 358/101
4,390,955 6/1983 Arimura ............................ 358/101

Primary Examiner—Howard W. Britton
Attorney, Agent, or Firm—Shapiro and Shapiro

[57] ABSTRACT

A pattern examining in which a pattern on an examined object such as reticle or mask is scanned to produce image binary signals of picture elements; binary information corresponding to a local area on the examined object is serially extracted from the image binary signals; and shape detection is effected for detecting by means of the binary information whether or not the pattern in the local area possesses a determined geometric shape or characteristics. The result of the shape detection is compared with the information on design relating to the geometric shape or characteristics which the pattern on the examined object should possess.

10 Claims, 23 Drawing Figures

FIG. 2
FIG. 3
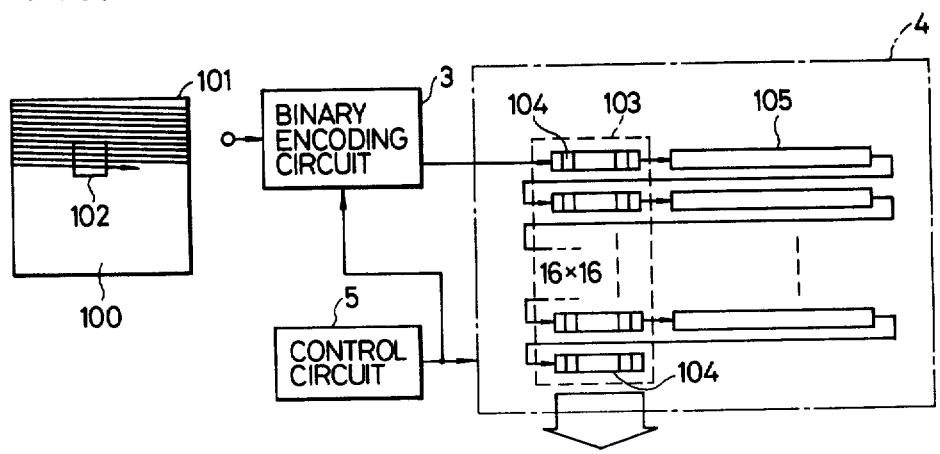
FIG. 4
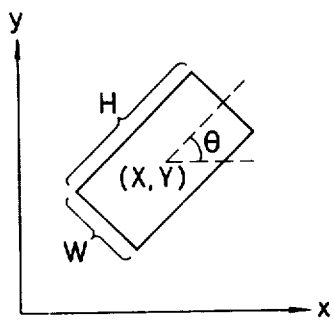
FIG. 5
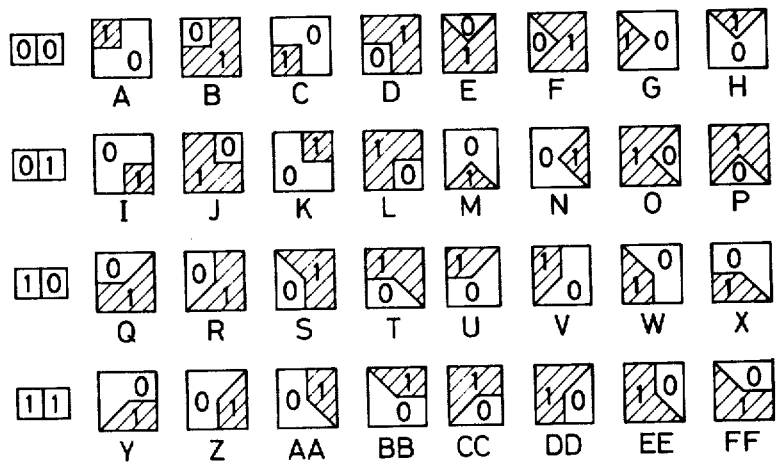

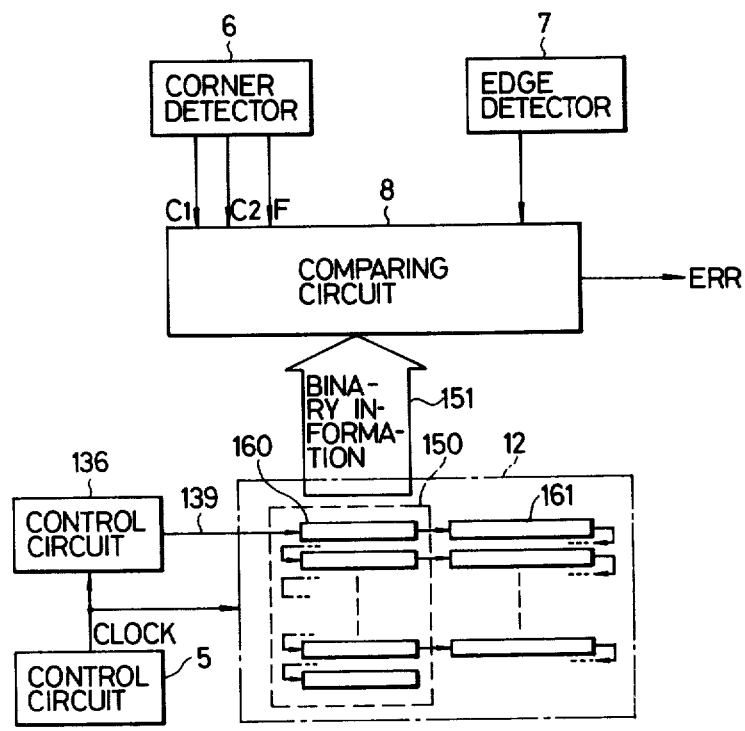
FIG. 15
FIG. 16a
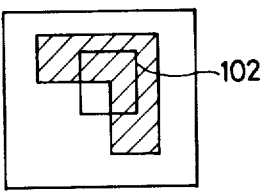
FIG. 16b
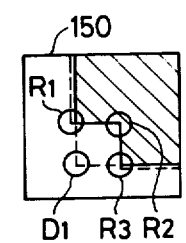
FIG. 17

APPARATUS FOR DETECTING THE DEFECT OF PATTERN

BACKGROUND OF THE INVENTION

1. Field of the Invention

The present invention relates to apparatus for examining a particular miniature pattern formed on a substrate to detect any defect contained in the pattern. More particularly, the present invention relates to a pattern examining apparatus in which the pattern transcribed onto a mask or reticle in the manufacturing process of integrated circuit (IC) is compared with the design data for forming the pattern to examine it whether or not the pattern has correctly been transcribed.

2. Description of Prior Art

For the above-mentioned type of pattern examining apparatus hitherto known there have been employed various comparing examination methods One of the known methods is the so-called chip comparison method according to which chips having the same patterns formed on the same mask are compared with each other.

Another well-known method is the so-called data comparison method. According to the method, design data are developed on an image memory as a bit pattern which is then compared with the image data obtained from the real pattern on the mask or reticle. The comparison is carried out picture element by picture element.

However, these known examination methods some drawbacks.

In the case of chip comparison method, if every chip has the same defect (common pattern defect), it is no longer possible to detect the defect. Further, the chip comparison method can not be used to examine a reticle pattern used as an original for making masks. This is because in many cases such reticle pattern exists alone.

As compared with the chip comparison method, the latter mentioned data comparison method has the advantages that it enables to detect even the common defect to chips and that it can be used also to examine the reticle pattern. The reason for this is that according to the data comparison method, the real image is compared with the corresponding design data. However, this data comparison method also involves some difficult problems. The problems are mainly attributable to the fact that a great deal of data must be stored in the image memory after converting the design data into image data of the individual picture elements. Thus, the image memory is required to have a very large capacity. The time required for input-output of the data to and from a computer becomes too long to be acceptable. Furthermore, it renders the examining apparatus large and complicate.

SUMMARY OF THE INVENTION

Accordingly it is the object of the invention to solve the above problems and provide such pattern examining apparatus which can rapidly judge the presence or absence of defect in the examined pattern without any need of large capacity memory means for storing a great deal of data while making a reference to the design data.

The apparatus to attain the object according to the present invention includes means for scanning a pattern on an examined object such as reticle or mask to produce image binary signals of picture elements; extracting means for serially extracting from the image binary signals such binary information corresponding to a local area on the examined object; and shape detection means for detecting it by means of the binary information whether or not the pattern in the local area possesses a determined geometric shape or characteristics. The result of detection by said shape detection means is compared with the information on design relating to the geometric shape or characteristics which the pattern on the examined object should possess.

According to one embodiment of the invention, the apparatus further includes edge detection means for detecting it by means of the binary information whether or not any edge portion of the pattern has appeared in the local area. According to the detection information from said edge detection means there is produced a defect information informing of the presence or absence of any defect in the pattern when the detection information from shape detection means agrees with the information relating to the geometric shape or characteristics on design.

Shape detection means which performs a function for relatively strict examination and edge detection means which performs a function for relatively loose examination cooperate each other in finding out any pattern defect. Therefore, according to the embodiment, the pattern can be precisely examined with high reliability even when the pattern has some delicate deformation at its edge portion. This is advantageous in particular when the pattern image in the form of picture elements is to be obtained by use of ITV or the like. The pattern image obtained by ITV or the like often has such corner deformed round. In such case, strict examination becomes less effective than loose examination for defect examination of pattern. For this reason, the accuracy in detecting pattern defect etc. can be improved very much by the combination of shape detection means and edge detection means according to the invention.

To attain the simple and errorless comparison of the above-mentioned determined geometric shape or characteristics of pattern according to the invention, the corners of a pattern detected in the local area are encoded according to the angle of the corner. This encoding is done according to the principle that such two corners having the same corner angle and being point-symmetric to each other be encoded with different codes each other.

According to the invention, information on design is represented as binary information. In another embodiment of the invention, the apparatus is provided with detection means for detecting by means of the binary information, the characteristics of pattern on design which should appear on the scanning line and for giving to the detected characteristics a determined binary code representative of said characteristics; and memory means provided with a determined number of bits, the number corresponding to the number by which the picture element on the scanning line is divided, and adapted to memorize the binary code by said detection means from the bit corresponding to the bit position where the characteristics of pattern on design should appear. The information relating to the characteristics of pattern on design is stored in said memory means in a compressed form.

In a further embodiment of the invention, the apparatus is provided with means for inhibiting the comparison examination. If there is any damage on the photo-reception surface of the image-pickup apparatus by which the pattern on the examined object is scanned, said inhibition means inhibits the examination of pattern by comparison as to the picture element corresponding to the damage. The damage on the photo-reception surface may be, for example, dust deposited on the surface or scratch on it.

According to a further embodiment of the invention, the alignment of the examined object can be attained by using image pattern data and design pattern data. The image pattern data are obtained by converting a pattern within a selected area of the object into image data. The design pattern data are design data from which the pattern has been formed. The positional deviation of the pattern image is detected based on the design pattern data. The alignment is performed by correcting the detected deviation. According to the embodiment it is no longer necessary to provide on the examined object any particular marks for alignment. Therefore, there is no need of particular optical system etc. for detecting the alignment mark.

Other and further objects, features and advantages of the invention will appear more fully from the following description taken in connection with the accompanying drawings.

BRIEF DESCRIPTION OF THE DRAWINGS

FIG. 2 is a schematic view of one picture area to be examined;

FIG. 3 is a detailed view of the extracting circuit 4 in FIG. 1;

FIG. 4 shows an example of design data recorded in the magnetic tape 9 in FIG. 1, the example being shown as a rectangular pattern on x-y coordinates;

FIG. 5 illustrates the manner of classification of corner patterns;

FIG. 15 is a view for explaining the operations of the extracting circuit 12 and the comparing circuit 8 during examination;

FIG. 16a illustrates an example of the corner information appearing in the reference window 150;

FIG. 16b illustrates a pattern corner appearing in the window 102;

FIG. 17 shows the reticle pattern corresponding to the area of the reference window together with its corner on design data;

FIG. 19b is an enlarged view of one picture area i shown in FIG. 19a;

DESCRIPTION OF PREFERRED EMBODIMENTS

Figure 1:
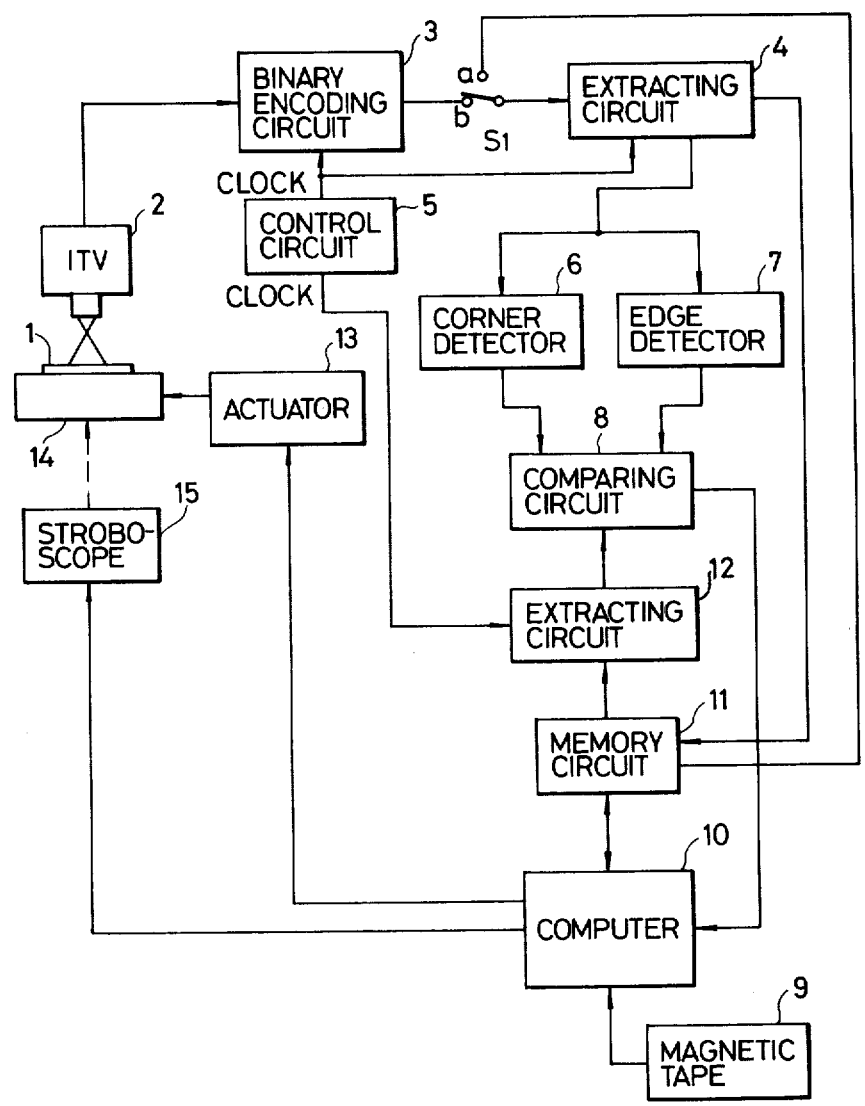
FIG. 1 is a block diagram showing an embodiment of the invention.

Referring to FIG. 1 showing an embodiment of the invention, an object to be examined is on a moving stage 14. The object is represented by a reticle 1 having a miniature pattern described thereon for the sake of explanation.

2 is an ITV by which only a determined small area on the reticle 1 is image picked up. The small area constitutes one picture to be examined. The reticle 1 is also illuminated by a stroboscope 15 in the manner of transmission illumination. The analogue image signal of ITV 2 is converted into a binary image signal by a binary encoding circuit 3. If necessary, smoothing or other processing for eliminating the noise may be carried out on the signal.

As shown in FIG. 2, one unit picture 100 to be examined is raster scanned by scanning lines 101 of ITV 2. In this embodiment, the number of scanning lines in one picture 100 is 1024 lines in the vertical direction.

From the binary image signal an extracting circuit 4 extracts binary data corresponding to a limited rectangular area in one picture. As an example, the limited area is shown to be a local area containing 16×16 picture elements.

Generally, the pattern on the reticle 1 is a pattern described in chrome on a glass plate. Therefore, the analogue image signal appears as a time-series signal corresponding to a bright and dark pattern, that is, a black-and-white image.

A control circuit 5 generates 1024 clock pulses per scanning line in the image 100. At every clock pulse, the binary encoding circuit 3 carries out the sampling of the analogue image signal to produce a picture element binary image signal.

FIG. 3 shows the detailed structure of the extracting circuit 4. 104 is a 16-bit shift register and 105 is a 1024-bit shift register. Two shift registers 104 and 105 are connected in series to form one step. The extracting circuit 4 comprises fifteen such steps connected in series each other and a further 16-bit shift register 104 as the last register of the serial register train. Therefore, the extracting circuit 4 is composes of a serial register train containing sixteen 16-bit shift registers and fifteen 1024-bit shift registers in total arranged as shown in FIG. 3. The binary image signal is introduced into the first 16-bit shift register 104 at first and then transferred serially into the serial register train in synchronism with the clock pulse from the control circuit 5. Since, as previously noted, the analogue image signal for one scanning line has binary encoded by 1024 times of sampling, the binary image signal obtained therefrom is a time-series signal representative of the binary logical value "0" or "1" of one picture element after dividing the picture 100 into 1024×1024 picture elements. After one sampling by the binary encoding circuit 3, the serial register train is shifted one time and the logical value of the picture element is transferred to the next bit. In this embodiment, the binary encoding circuit 3 carries out the sampling of one scanning line with 1024 clocks. During the period of retrace line subsequent to the above scanning, it carries out the sampling with 16 clocks. The extracting circuit 4 is also shifted 16 times during the period of retrace line. Thus, the extracting part 103 composed of sixteen shift registers 104 has binary picture element data of the local area 102 registered therein. As previously described, the area 102 registered therein. As previously described, the area 102 is a local rectangular area containing 16×16 picture elements of the picture 100. Hereinafter, this area 102 is referred to as window 102. With the proceed of scanning, the window 102 is moved within the picture 100 at the rate of one picture element per one clock pulse so as to serially extract binary picture element data from the whole area of the picture 100.

The binary data of 16×16 picture elements extracted by the window 102 in this manner are introduced into a corner detector 6 and an edge detector 7 as shown in FIG. 1. The function of the corner detector 6 is to detect the edge appearing in the window 102 and corresponding to the boundary between the bright part and the dark part of the pattern on the reticle 1. When the edge is coincident with a certain previously prepared corner pattern, the corner detector issues an information output selected from four different kinds of information according to the detected edge. The four different kinds of information are previously prepared by classifying the corner patterns into four groups in regard to the shape and direction thereof. The function of the edge detector 7 is to detect the presence of an edge in window 102 which is probably a corner pattern even when the corner detector 6 fails to detect it because the corner pattern on the reticle 1 has been somehow rounded by an effect of the image-pickup optical system.

On the other hand, the design data used in making the pattern on the reticle 1 have previously been stored in a magnetic tape 9. The design data is read into a computer 10 from the magnetic tape 9. The design data stored in the magnetic tape 9 cover the entire surface area of the reticle. For example, the design data are stored as a set of rectangular patterns as shown in FIG. 4. In practice, a circuit pattern actually formed is a complicated assembly of such rectangular patterns. As shown in FIG. 4, one rectangular pattern is represented by five parameters, width W, height H, the coordinate of the center (X, Y) in a determined x-y coordinate system on the reticle and rotation angle $\theta$.

Referring again to FIG. 1, the computer 10 puts out the design data corresponding to one picture area on the reticle 1 picked-up by ITV 2. The output design data is applied to a memory circuit 11 which then detects only the corner pattern from the design pattern and extracts the corresponding corner information from the four different information classified in the manner described above to keep the extracted corner information in memory simultaneously with the above detection by the corner detector 6.

The memory circuit 11 serially stores the corner information existing in one design picture while extracting them from the design data in line with the movement of the above window 102. In this manner, all the corner information of the corner patterns existing in one picture are stored in the memory 11. The corner information for one picture are stored in a memory (not shown) within the computer 10 as data of one picture. During the time, the computer 10 carries out the output of the design data for the next one picture.

All of the operations described above for the extraction of corner information from the design data, the storage of the corner information in the memory circuit 11 and the transfer of the corner information from the memory 11 to a memory in the computer 10 are carried out prior to the real comparative examination later described. After all the corner pattern information relating to all the pictures on the reticle 1 have been stored in the memory within the computer 10, an examination of the pattern on the reticle 1 is actually started.

At the start of the actual examination of pattern, the computer 10 controls an actuator 13 to align the stage 14 with one picture area on the reticle 1. The actuator 13 is movable two-dimensionally for positioning the stage 14. Thus, the stage 14 is brought into alignment with one picture area to be image-picked up. At the same time, the computer 10 transfers the corner information for the one picture area from its memory to the memory circuit 11.

The corner information are serially transferred to an extracting circuit 12 from the memory circuit 12. The extraction area by the extracting circuit 12 is preset to be smaller than the above-mentioned window 102. The extracting circuit 12 serially extracts the corner information based on the design data in synchronism with the clock pulse from the control circuit 5.

Since, as previously noted, the window 102 is moved in one picture with the clock pulse from the control circuit 5, the extraction area by the extracting circuit 12 (hereinafter this extraction area is referred to as reference window) and the above window 102 moves in the same direction in synchronism with the clock pulse.

The output corner information from the corner detector 6, the output detection result from the edge detector 7 and the output information from the extracting circuit 12 are all applied to a comparing circuit 8. When the real pattern on the reticle and the pattern in the design data are different from each other, the comparing circuit 8 produces out a defect information signal to the computer 10. More concretely, when the information in the reference window contains at least one corner information of the same kind as that of the corner information from the corner detector 6, it is regarded as no defect. Also, when the edge detector 7 detects in the window 107 any corner pattern-like edge or any simple linear edge at the time point at which a corner information comes into the center portion of the reference window, it is regarded as no defect.

In this manner, the comparing circuit 8 serially makes comparison between the corner information derived from one picture then image-picked up and the corner information stored in the memory 11 and produces out a defect information to the computer 10 in real time. This comparing operation is carried out throughout the entire area of the reticle up to the completion of the examination on one sheet of reticle.

The manner of control on the stroboscope 15 will be described in detail later.

Before beginning a detailed description of the corner detector 6, we will describe the characteristics of IC patterns for better understanding of the invention.

In general, an IC pattern is formed by suitably assembling a plurality of rectangular patterns into a pattern.

One example of such rectangular pattern element is shown in FIG. 4. Further, IC pattern is usually so formed that the rotation angle $\theta$ of every rectangular pattern element is 45° or 135° relative to the x-y coordinate system on the reticle. It is very seldom that the rotation angle $\theta$ is any other angle than 45° and 135°. Based on the fact we can consider that the possible corner angles of the corner patterns formed by any combination of such rectangular pattern elements on design or on the reticle 1 are limited to 90° and 135° only.

FIG. 5 illustrates various corner patterns.

Thirty-two squares A to FF shown in FIG. 5 are extraction areas by the extracting circuit 4. Therefore, each the square corresponds to the window 102. In every square, the hatched portion means the area of logic "1" corresponding to the chrome surface area and the blank portion means the area of logic "0" corresponding to the glass surface area by way of example. Since, as previously noted, the corner angles of corner patterns may be limited to 90° and 135° only, the kinds of corners which may appear in the window 102 can be limited to only thirty-two different kinds shown in FIG. 5. These thirty-two corners may be classified in various manners. It is not impossible to give thirty-two different codes to the thirty-two corners respectively. However, if such a classification method is employed, there are required five bits ($2^5=32$) for binary encoding. Therefore, according to a preferred embodiment of the invention, these thirty-two kinds of corners A to FF are classified into four groups as shown in FIG. 5. The classification has been done according to the following principle:

At first, they are divided into two groups, a group of those corners which have the corner angle of 90° and a group of those of 135°. Thereafter, the group of 90° is further divided into two groups and also the group of 135° is further divided into two groups. The second classification is made in such manner that two corners symmetrical to each other with regard to the center of the window 102 (with regard to the picture element at about the center of the extracted 16×16 picture elements) are not included in the same group, and that two corners of the same corner angle which have an inverted relation to each other are included in the same group. For example, A and B are classified into the same group because they are in inverted relation to each other whereas A and I are classified into different groups because that are symmetrical to each other with regard to the center of the window. In this manner, the thirty-two corners A to FF have been classified into four groups represented by binary codes, 00, 01, 10 and 11, namely the first group encoded with 00 which contains the eight corners A to H having the same corner angle of 90°, the second group with binary code 01 containing the eight corners I to P having the same corner angle of 90°, the third group with binary code 10 containing the eight corners Q to X having the same corner angle of 135° and the fourth group with binary code 11 containing the eight corners Y to FF having the same corner angle of 135°.

The reason why the corners having the same corner angle (for example, B and L) are classified into different groups according to the relation of point-symmetry is concerned with the mode of corner defect and the operation of comparison of the comparing circuit 8, which will be described later.

To corner detector 6 is provided with the above thirty-two corner patterns as reference patterns (so-called ten-plate) and carries out matching of the reference patterns with the patterns appearing in the window 102 (bit patterns).

Figure 6:
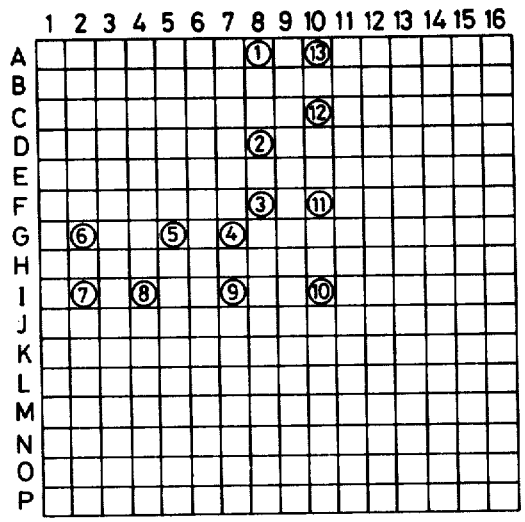
FIG. 6 shows 16×16 bits corresponding to the window extracted by the extracting circuit 4.
Figure 7:
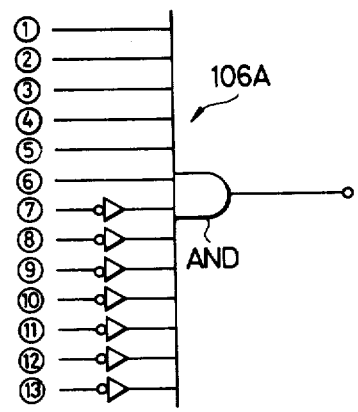
FIG. 7 shows AND-gate circuit for detecting the corner A shown in FIG. 5.

FIG. 6 illustrates 16×16 bits by the above-mentioned 16-stage registers 104 corresponding to the window 102 by the extracting circuit 4. By way of example, the corner A or B shown in FIG. 5 is now detected. The thing necessary for the detection of A or B is to examine the respective logical values of bits ①  to ⑥ and bits ⑦ to ⑬ among 16×16 bits in FIG. 6. To detect the corner A there is used an AND gate circuit as shown in FIG. 7. The AND gate issues out an output of "1" only when the inputs ① to ⑥ are all "1" and the inputs ⑦ to ⑬ are all "0". To detect the corner B, the inverters are disconnected from the inputs ⑦ and ⑬ instead inverters are connected to the input ① to ⑥.

Thirty-two such AND gates are provided for the thirty-two corner patterns respectively so that binary data are applied to inputs of AND-gate from the determined bits corresponding to the reference pattern among 16×16 bits of the extracting circuit 4.

Figure 8:
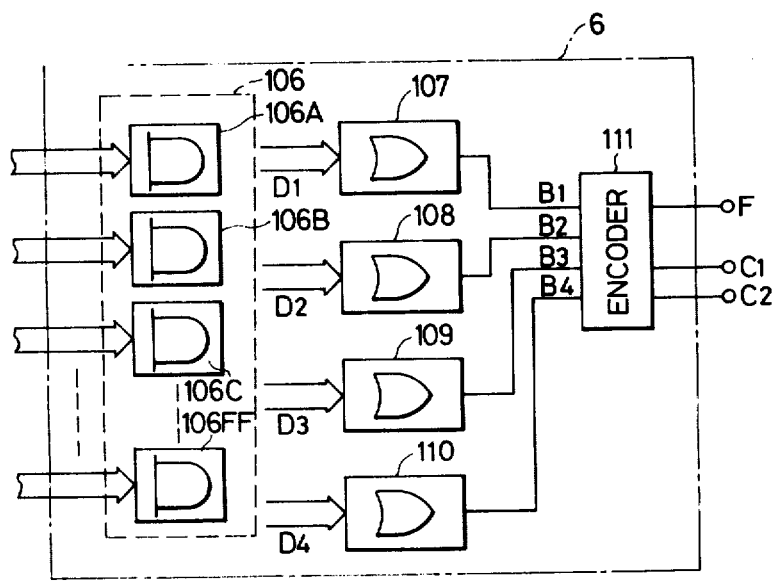
FIG. 8 shows the corner detector for detecting the corner by AND-gate circuit as shown in FIG. 7 and producing an output of 2-bit code.

FIG. 8 shows the detailed construction of the corner detector 6 which detects a corner by an AND gate circuit as shown above and issues out a 2-bit code.

In FIG. 8, 106 is a matching circuit composed of thirty-two AND gates 106A to 106FF each of which has an output of logic "1" when it detects the corresponding one of thirty-two corners A to FF. Applied to the input of each the AND gate circuit are binary data from extracting part 103 of the extracting circuit 4.

Thirty-two output signals from the matching circuit 106 are classified into four groups. Outputs from the eight AND gates for detecting the corners A to H are grouped into an 8-bit data $D_1$, outputs from the eight AND gates for detecting the corners I to P are grouped into an 8-bit data $D_2$, outputs from the eight AND gates for detecting the corners Q to X are grouped into an 8-bit data $D_3$ and outputs from the eight AND gates for detecting the corners Y to FF are grouped into an 8-bit data $D_4$. These four 8-bit data $D_1$, $D_2$, $D_3$ and $D_4$ are applied to OR gate circuits 107, 108, 109 and 110 respectively. The four output signals from the four OR gates are introduced into an encoder 111 which encodes the input 4-bit binary signals and puts out its code as a 2-bit code $C_1$, $C_2$.

The manner of operation of the above circuit is as follows:

When there appears in the window 102, for example, the corner C shown in FIG. 4, then among the thirty-two AND-gates in the matching circuit 106 only one AND-gate 106C has an output of logic "1" and the remaining AND gates are all "0" in output. Therefore, of eight bits in data $D_1$ only one bit is "1" and other seven bits are all "0". The output from OR gate 107 is "1" and outputs from other three OR gates 108, 109 and 110 are all "0". Thus, the encoder 111 has "1" at input $B_1$ and "0" at other inputs $B_2$, $B_3$ and $B_4$. A binary number obtained by subtracting 1 from the binary number of the binary signals encoded is issued from the encoder 111 as a 2-bit code, $C_1$, $C_2$. For this example where corner C is detected, the output from the encoder 111 is $C_1$, $C_2=00$.

As another example, when the corner FF appears in the window 102, the code, $C_1$, $C_2=11$ because the encoder 111 has "0" at inputs $B_1$ to $B_3$ and "1" at input $B_4$. When any one of the inputs $B_1$ to $B_4$ becomes "1", the encoder 111 issues out also flag F which is "1" when any corner is detected and "0" when no corner is detected.

Figure 9:
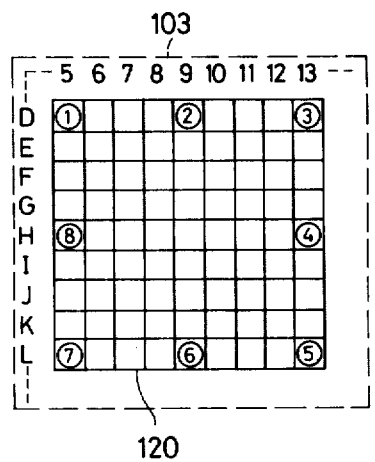
FIG. 9 shows the rectangular area of 9×9 picture elements set for the detection of edge.

FIG. 9 illustrates a rectangular area of 9×9 picture elements set for the edge detection by the edge detector 7. This rectangular area 120 lies at about the central portion of the area of 16×16 picture elements mentioned above. Therefore, the edge detector 7 carries out the edge detection based on the information derived from the area 120 composed of 9×9 bits among the extracting part 103 of 16×16 bits for extracting 16×16 picture element data shown in FIG. 3. The center bit of the area 120 (which corresponds to the center picture element) is positioned at (H, 9) regarding 16×16 bits shown in FIG. 6. The bits to be particularly regarded at for the edge detection are eight bits (1) to (8) located at every four bits along the periphery of 9×9 bits shown in FIG. 9.

Figure 10:
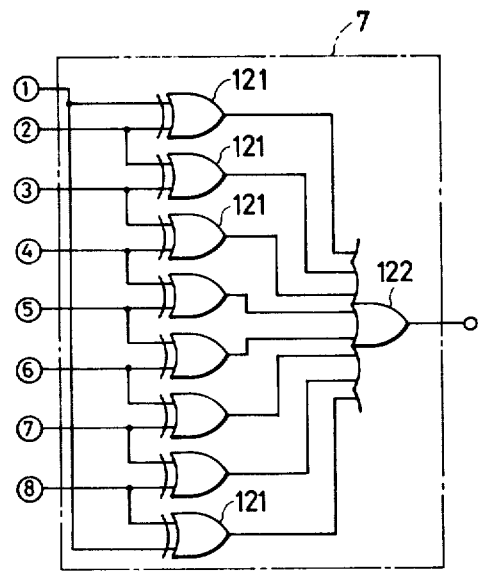
FIG. 10 is a circuit diagram of the edge detector.

FIG. 10 is a detailed circuit diagram of the edge detector 7.

As shown in FIG. 10, the edge detector 7 includes eight exclusive OR circuits 121 to which are applied binary signals from the particularly appointed eight bits (1) to (8) arranged along the periphery of the area 120. When even one of the eight bits is different from other bits in logical value, then OR gate circuit 122 puts out logic "1" which informs of the fact that some edge has been detected. The two input terminals of each of the eight exclusive OR circuits 121 are connected to the corresponding two neighbouring bits of the particularly appointed eight bits (1) to (8) in the area 120 as seen in FIG. 10.

Figure 11:
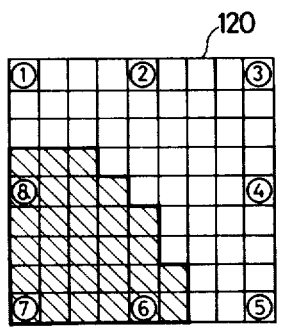
FIG. 11 shows a pattern appearing in the 9×9 bit area.

The manner of operation of the edge detector 7 is as follows:

If there appears in the area 120 some thing which is probably an edge as shown in FIG. 11, then the logical value becomes "1" in the hatched area exclusively. In this case, of the inputs to the edge detector 7 the inputs (1) and (8) have different logical values from each other and also the inputs (5) and (6) have different logical values. Therefore, OR gate 122 puts out logic "1". Even when a simple linear edge appears in the area 120, the edge detector operates in the same manner as above and also logic "1" is put out from OR gate 122.

The above edge detector 7 operates in real time during the examination of reticle and simultaneously with the scanning by ITV 2. If it is desired to more surely detect the appearance of any edge, it may be attained by introducing the binary signals of all of 32 bits along the periphery of 9×9 bit area into the inputs of the edge detector 7. In this case, when all of the thirty-two bits have the same logical value, it means that there is no pattern edge. If even only one of the thirty-two bits has a different logical value from other bits, then it is indicative of the detection of some edge.

Figure 12:
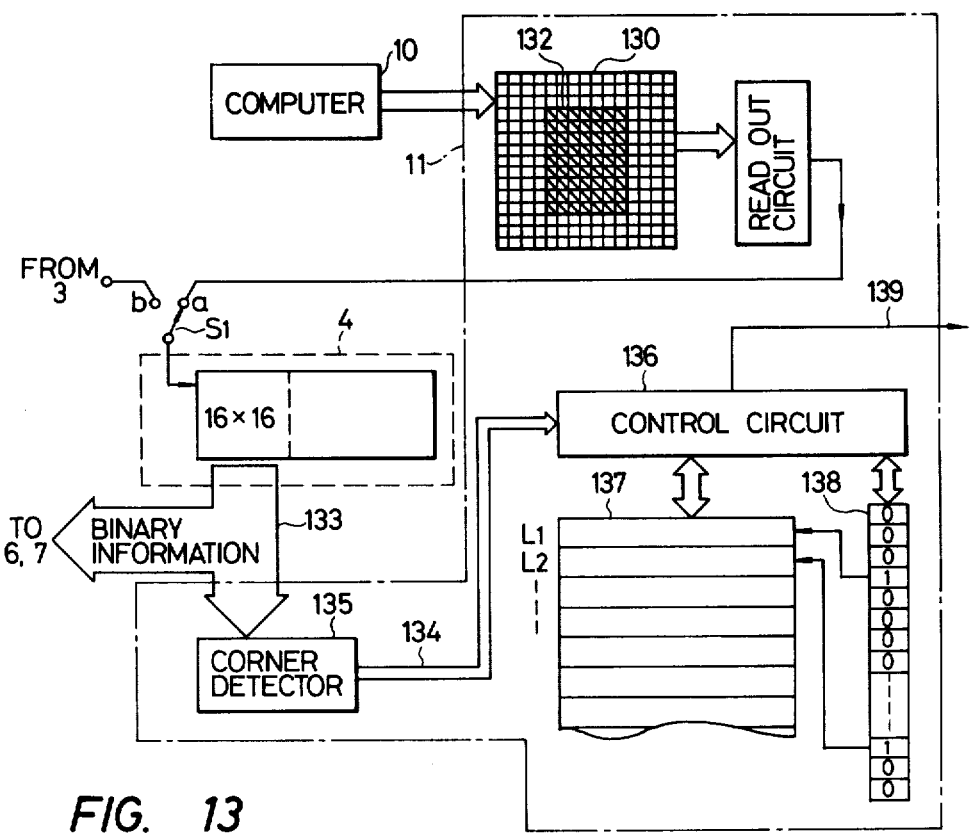
FIG. 12 is a diagram showing the detailed construction of the memory circuit.

Referring now to FIG. 12 there is shown the detailed structure of rhe memory circuit 11 which reads the design data from the magnetic tape 9 shown in FIG. 1 and holds the data therein.

The memory circuit 11 includes a 1024×1024 bit frame memory 130 and a readout circuit 131. The frame memory 130 receives the design data from the computer 10 and converts the design data into binary images of "0" and "1" as the design pattern corresponding to one picture. The readout circuit 131 reads out the binary signals in time series according the sequence of scanning by ITV 2. S1 is a switch which can be switched over from terminal a for non-examination to terminal b for examination and vice versa. Applied to the terminal b is the binary image signal from the binary encoding circuit 3.

The above-described extracting circuit 4 takes up from the output signal of the readout circuit 131 the binary information 133 of the local rectangular area in the frame memory 130. The rectangular area in the frame memory 130 is very good in the linearity of the boundary between "1" and "0" and also sharp in the corner. This is because the bit pattern formed in the frame memory 130 is based on the design data. Therefore, the rectangular area can be taken up from a smaller area than the area of 16×16 bits in the extracting circuit 4. The binary information 133 thus taken up are applied to a detector 135 by which the binary information are classified into four groups. The structure of the detector 135 is substantiall the same as that of the previously described corner detector 6. The output of the detector 135 comprises classification codes (00, 01, 10, 11) and a flag to indicate it whether or not any corner is detected.

136 is an input-output control circuit which receives the output 134 from the detector 135. Under the control by the control circuit 136, the codes are registered in a reference data memory 137 and the flag is registered in a flag memory 138. This operation of registration is carried out during the time of non-examination. At the time of examination, the switch S1 is connected to the terminal b and the output information from the extracting circuit 4 are introduced into the previously described corner detector 6 and edge detector 7. At the same time, the control circuit 136 puts out reference data 139 the content of which is the codes previously registered in the reference data memory 137 and the flag previously registered in the flag memory 138.

All of the readout circuit 131, control circuit 136 and extracting circuit 4 operate on the basis of the clock pulse generated from the control circuit 5 shown in FIG. 1. The reference data memory 137 holds the corner information of only the row of bits where a corner exists and extends in the horizontal direction (scanning direction) within the frame memory 130. The flag memory 138 is composed of the same number of bits as the number of bits in the vertical direction of the frame memory 130 (in this embodiment, the number of bits is 1024). When a corner appears in any of horizontal bit rows (1024 rows), "1" is set to the corresponding bit or bits of the flag memory 138 and "0" is set to other bits where no corner is present. These operations are all executed by the control circuit 136.

The manner of operation of the reference data memory 137 for holding the corner information will be described hereinafter with reference to FIG. 13.

Figure 13:
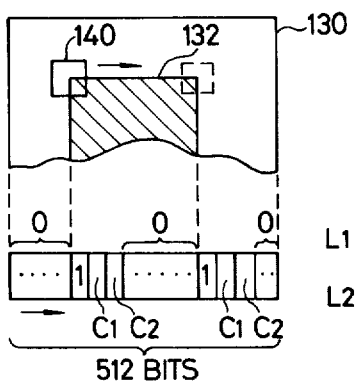
FIG. 13 shows the frame memory in the memory circuit.

The binary information 133 extracted by the extracting circuit 4 corresponds to the rectangular area (window) 140 shown in FIG. 13 The window 140 scans the frame memory 130 in the direction of arrow. In the reference data memory 137 there are provided 512 bits for one horizontal scanning. (These 512 bits are hereinafter referred to as one line memory).

As the window 140 scans the frame 130 in the direction of arrow, in FIG. 13. the flag of the detector circuit 135 is "0" at the beginning of the scanning because there is no corner in the portion. Therefore, "0" is written in the beginning portion of the one line memory. In this connection, it is to be noted that one binary logic is registered in one bit of the line memory every time of two bits being scanned by the window 140 and that the bit in which the binary logic is registered is one bit shifted from the now scanned bit. Thus, the one line memory holds information of horizontal 1024 bits of the frame memory 130 in the form compressed into ¼.

After a further advance of the scanning, the window 140 catches the left-hand upper corner of the pattern 132. At the time, "1" indicative of the presence of corner is registered in the corresponding bit of the one line memory. A code $C_1$, $C_2$ issued from the detector circuit 135 is also registered in two bits next to the bit. For the part where no corner is present, "0" is written in the corresponding bits of the one line memory. In this manner, when the window 140 has completed one scanning of the corner existing portion, there are obtained the reference data for one line.

Figure 14:
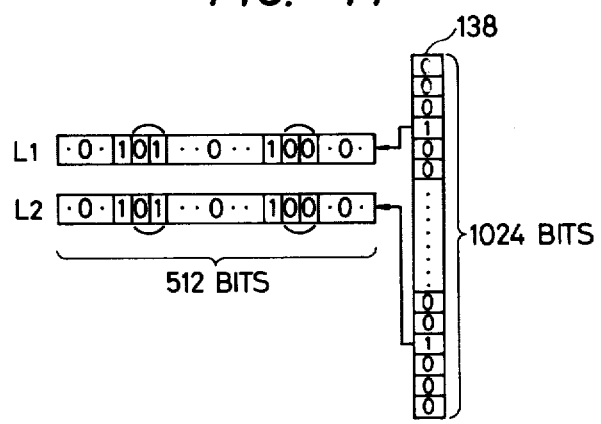
FIG. 14 shows the information registered in the reference data memory 137 and the flag memory 138 when there is present a bit pattern 132 in the frame memory.

As a concrete example, FIG. 14 shows the information stored in the reference data memory 137 and the flag memory 138 in the case where a binary image bit pattern 132 based on the design data exists in the frame memory 130 shown in FIG. 12. In this case, the bit pattern 132 has four corners whose corner codes are produced out from the detector 135 in accordance with the classification shown in FIG. 5. The corners of the bit pattern in the frame memory 130 are present in only two horizontal bit rows. Therefore, in the reference data memory 137, only two one-line memories $L_1$ and $L_2$ have the reference data registered therein. On the other hand, in the flag memory 138, "1" is set to only two bits corresponding to the two horizontal bit rows in the frame memory 130. To all other bits of 1024 bit flag memory 138, "0" is set. Thus, the flag data for one picture are prepared in the flag memory. While the reference data memory 137 and the flag memory 138 have been shown to hold only the area corresponding to one picture of 1024×1024 bits, in practice such reference data and flag data are prepared for every picture on the reticle prior to the defect examination of reticle based on the input of the image signal by ITV 2, and these data are stored in the memory of the computer 10. Therefore, for an instance, when the defect examination is to be carried out while dividing the entire area of the reticle into 10×10 sections, that is, 100 pictures, the memory for flag data is required to have a memory capacity of the fixed bit length for 1024×100 bits. Also, the memory for reference data is required to have a memory capacity of the same number of 512 bit one-line memories as the number of logic "1" bits in the flag memory 138. Therefore, if the number of "1" in 1024×100 flag memory 138 is 1000, then the capacity required for the memory for reference data is 512 bits × 1000 lines.

The control circuit 136 controls the reference data memory 137 and the flag memory 138 on the basis of the output 134 from the detector 135 so as to register the data in the memories in the manner described above. During the time of examination, the control circuit 136 controls the memories 137 and 138 to make them put out the registered data serially as the reference information 139. Where the flag of the flag memory 138 is "0", the reference information 139 puts out "0" for 512 bits. Where the flag is "1", the reference information puts out the data for one line of the reference data memory 137 corresponding to the flag in time series.

During the examination, the corner information extracting circuit 12 and the comparing circuit 8 shown in FIG. 1 are in operation. Now, the structure and operation of the extracting circuit 12 and the comparing circuit 8 will be described with reference to FIG. 15.

The corner information extracting circuit 12 is composed of an array of serially connected shift registers. Designated by 160 are 10-bit registers in nine stages which constitute together a reference window 150. Designated by 161 are 512-bit registers series-connected to the 10-bit registers 160 respectively. The reference information 139 from the control circuit 136 are introduced into the first 10-bit register 160 of the serial shift register array and then shifted bit by bit in the shift register array in synchronism with clock pulse from the control circuit 5. In practice, the timing of shift is so selected as to shift it once per two clocks. Binary information 151 of the reference window 150 covering 90 bits (10×9 bits) are introduced into the comparing circuit 8 as they are.

The manner of operation of the control circuit 136, extracting circuit 12 and comparing circuit 8 is as follows:

Prior to the output of the first clock of one horizontal scanning line from the control circuit 5 shown in FIG. 3, the control circuit 136 examines it whether the flag of the bit corresponding to the scanning line in the flag memory 138 is "0" or "1". If it is "1", then it puts out the reference data (512 bits) for the one line in the reference data memory 137 in the rate of one bit per two clocks serially as the reference information 139. If the flag is "0", the control circuit 136 puts out 512 bits of "0" at every two clocks as the reference information 139 during the horizontal scanning (1024 clocks). These outputs are serially shifted through the serial shift register array. During the time of retrace line of ITV 2, there are generated, as the reference information 139, 10 bits of "0" and the shift register array is shifted also ten times. In this manner, in response to the start of examination, the reference data in the memory 138 are serially extracted by the reference window 150. At the start of examination, the corner detector 6 and the edge detector 7 are also brought into operation to produce the corner information of the pattern on the reticle.

FIG. 16a shows an example of corner information appearing in the reference window 150. For the sake of explanation, the bit positions of 10×9 bits contained in the rectangular reference window 150 are represented by (x, y). In FIG. 16a, the rows of bits extending in x-direction at y=4 and y=8 are logical values derived from the reference data. At other positions of y, the rows have logic "0" because of the flag being "0" for these other rows of bits which are indicated by the mark "." in FIG. 16a.

As previously mentioned, the window 102 also moves in one picture of the reticle pattern image-picked up as shown in FIG. 2, in synchronism with the extracting operation of the extracting circuit 12. When the window 102 catches a pattern corner as shown in FIG. 16b, the corner detector 6 sets "1" to flag F and produces out $C_1 C_2 = 0. 0$ as the code.

The comparing circuit 8 examines the binary information 151 of the reference window 150 when it detects "1" of the flag F. The comparing circuit 8 examines all of the binary information 151 from (x, y)=(1, 1) to (x, y)=(10, 9) bit by bit to find out the bit which is "1". When it is found out, the comparing circuit 8 makes a comparison between the logical values of two bits subsequent to the bit and the code issued out from the corner detector 6. If the code does not exist in the reference window 150 at all, then the comparing circuit generates an information signal ERR to inform that there is a defect in the pattern on the reticle. This comparison is possible only when the corner pattern has been formed on the reticle in a steady and detectable manner. If the corner pattern has been formed unsteadily, the corner detector may fail to detect it. In this case, the corner detector 6 has no output of the flag F and therefore no comparison is carried out by the comparing circuit. This results in a misjudgement that no corner is present at the corresponding position on the reticle. To avoid such misjudgement by the detector there is provided the edge detector 7. When the center bit of the reference window 150, for example, the bit at (x, y)=(6, 5) is "1" which means the presence of a corner at the position on the design data, and when the edge detector 7 detects some edge and its result is "1", then the comparing circuit 8 also generates a defect information signal ERR. This defect (or error) signal contains not only the information of presence or absence of defect but also information relating the position of the existing defect. The information of the position of the existing defect can be obtained in a simple manner by counting the clocks from the control circuit 5.

The classification method of corners previously described for the corner detector 6 is related to the above comparing method. The relation will be explained hereinafter with reference to FIG. 17.

In the area of the reference window 150 shown in FIG. 17, the hatched portion is a real pattern on the reticle. The dotted line indiates the corresponding pattern on design. The pattern on design has a corner D1 which is missing in the real pattern on the reticle. Thus, the real pattern has a defect that a portion of the corner is missing. Because of the defect, the real pattern on the reticle has three corner patterns R1, R2 and R3. According to the classification described above, the classification codes given to these three corner patterns are: R1 (0 1), R2 (0 0) and R3 (0 1). In contrast, in the reference window 150, there exists only D1 (0 1) as the code of the corner pattern on design.

As the comparing circuit 8 operates in the manner described above, it can detect the defect when the corner pattern R2 is detected. The reason for this is that in the reference window 150 there is no such code which is the same as that of the corner pattern R2.

The detection of a defect as shown in FIG. 17 becomes possible by employing the above described method for corner classification according to which a corner pattern as R1, R3 and a corner pattern as R2 are classified into different groups and encoded with different codes. This classifying method has an advantage that any defects can be detected by use of few codes even for such case where the real corner pattern on the reticle has a portion missed out or deformed in the area corresponding to the reference window 150.

As described above, the comparing circuit 8 examines the flag and codes existing in the reference window 150 when codes are issued from the corner detector 6. Therefore, even when there occured a small deviation of the area of one picture picked up by ITV 2 from the area on design predetermined by the design data, it is possible to perform the examination of pattern without need of correction for such deviation.

In the embodiment of the invention, the matching circuit in the corner detector 6 takes up the necessary binary signals for detecting a corner pattern from thirteen bits, ①to ⑬ among 16×16 bits as shown in FIG. 6. This brings forth the following advantage:

As shown in FIG. 6, the bits to be taken up among 16×16 bits are those which the edge of the bit pattern passes through. For example, when the bits① and ⑬ or bits⑥ and ⑦ are picked up, there is given an allowance in the amount of one bit between① and ⑬ or⑥ and⑦ This allowance is significant because a bit pattern image-picked by ITV or the like and then binary-encoded is generally not smooth but rough in the form of straight lines thereof. The one bit allowance permits such roughness of the bit pattern while preventing such roughness from interferring with the corner detection.

Figure 18:
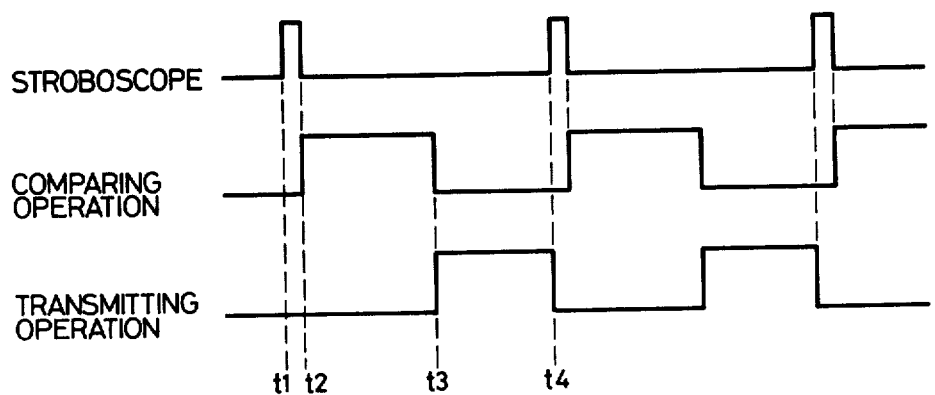
FIG. 18 is a timing chart of flashing of stroboscope, comparing operation and data transmitting operation.

Although not shown in the above embodiment, the two-dimensional position of the stage 14 is continuously measured as coordinate value by an optical interferometer or the like. The measured coordinate value of the stage 14 is applied to the computer 10. When the reticle 1 is image picked up by an image-pickup apparatus, for example, ITV 2 to start the examination actually, the computer 10 contrcls the actuator 13 according to the measured coordinate of the stage 14. The stage 14 is moved in such manner that after completing the image-pickup of one picture area in the reticle 1 by ITV 2 and the following comparing operation described above, the next picture area can be image-picked up. At the time, the input of one picture picked-up by ITV 2 is carried out by flashing of the stroboscope 15. The manner of input of the image will be described hereinafter with reference to FIG. 18.

When the one picture area on the reticle 1 to be examined is correctly positioned just under ITV 2, the computer 10 judges the position of the stage 14 to be correct from its coordinate value and generates a flash start signal to the stroboscope 15 at a time point t1. At t2, the photoreception surface of ITV 2 is electrically charged according to the pattern image of the area to be examined. From the time point t2, ITV2 starts scanning and also the comparing operation is started. Therefore, the code derived from the reference data in the memory circuit 11 and the code produced from the corner detector 6 are compared with each other by the comparing circuit in the manner described above. Thus, the examination of one picture is started. At t3, the examination for the first one picture is completed. During the period from t3 to t4, data for the next one picture (reference data and flag) previously stored in the memory within the computer 10 are transferred to the reference data memory 137 and the flag memory 138 in the memory circuit 11. Upon the completion of data transfer at t4, the computer 10 again applies a flash start signal to the stroboscope 15. During the data transfer period from t3 to t4, the residual image on ITV2 is erased. During the period from t2 to t4, the stage 14 with the reticle 1 thereon is moved to the determined position for the image-pickup of the next picture area by ITV2.

The above operation is repeated many times to examine the entire area of the reticle 1.

As readily understood from the above, the input of image by ITV2 is performed only at the flash time of the stroboscope 15. Therefore, in practice, it is not always necessary to stepwise move the stage 14. It is possible to continuously move the stage while suitably controlling the moving speed. In this case, the output of a flash start signal from the computer 10 may be done when the coordinate value of the stage 14 measured by the optical interferometer reaches the value determined for the next picture area of the reticle 1. As another modification, it is also possible to move the stage 14 at uniform speed and to make the stroboscope 15 flash at regular time intervals according to the speed. In this case, all of the operations for examination by comparison, data transfer and erasing the residual image may be carried out completely during the interval from one flash to the next flash. This enables to carry out the examination at a higher speed as compared with the case where the stage 14 is stepwise moved.

For the above described embodiment it is required to make the coincidence of one picture area picked up by ITV2 and the area on design prepared for the one picture area based on the design data. To attain it, when a reticle 1 is placed on the stage 14, the rotational deviation of the reticle 1 is corrected and also the origin of the coordinate of the stage is set. The operation necessary for this will be described hereinafter with reference to FIG. 19.

Figure 19A:
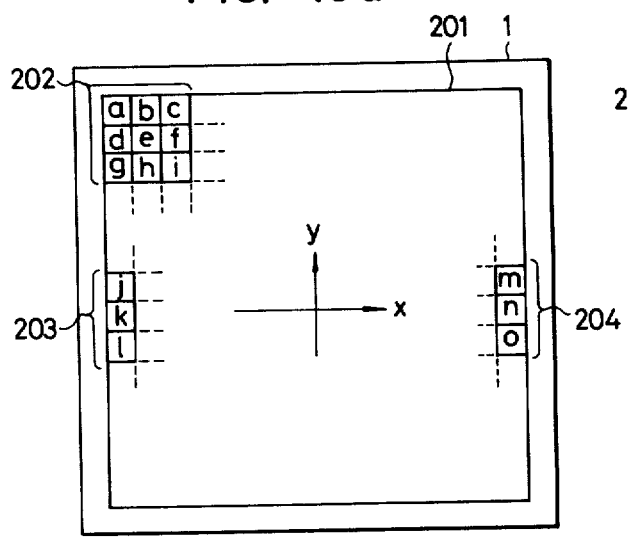
FIG. 19a shows the pattern bearing area of a reticle divided in matrix.

In the matrix shown in FIG. 19a, each square corresponds to each one picture area to be image-picked up by ITV2. At first, a reticle 1 is placed on the stage 14 while roughly aligning each other. Thereafter, the stage 14 is two-dimensionally moved to set the origin of the coordinate. This setting of the origin is performed by clearing a counter (not shown) in the actuator 13 to zero. The content of the counter represents the coordinate of the stage 14 and its count is increased up and decreased down with the movement of the stage 14.

The origin of the coordinate is determined using an area 202 lying at one corner of the area 201 where a pattern has been described. The area 202 used for determining the origin covers, for example, 3×3 pictures. Of course, the origin may be determined using only one picture area a at the left and upper corner. However, there may be such case where no pattern has been formed at the area a. In this case, the origin can not be determined. Taking into consideration such a case, in this embodiment, the area 202 covering 3×3 pictures, that is, nine picture areas a to i is prepared for determining the origin. In setting the origin, any suitable one selected from the nine picture areas is used for it.

Figure 19B:
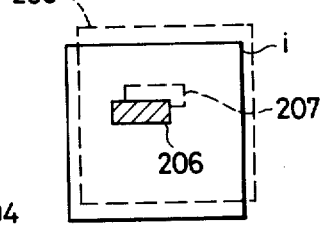

For example, if the picture area i has some pattern 206 described therein as shown in FIG. 19b, the picture area i is employed as the origin. In FIG. 19b, the solid line indicates the real picture area i on the reticle to be image-picked up by ITV 2. The broken line 205 indicates the picture area i on design.

Design data corresponding to the picture area i are read out from the computer 10 as described above, and the pattern designed is developed in the frame memory 130 of the memory circuit 11 shown in FIG. 12 as a bit pattern. Then, the time-series binary signals from the read out circuit 131 are introduced into a image reproducer, namely, a monitor television to reproduce on the screen of the monitor TV the area on design 205. At the same time, the image signals of ITV 2 on the same screen of the monitor TV to observe the real pattern 206 on the reticle 1 and the pattern on design 207 in an overlapped state.

Since the real pattern 206 moves in the TV screen with the movement of the stage 14, the setting of the origin in practice is performed by moving the stage 14 to the position in which the real pattern 206 and the pattern on design 207 are correctly overlapped each other. At this position, the above-mentioned counter is cleared to set the origin of the coordinate.

After setting the origin, a minute rotational error of the reticle 1 is corrected in the following manner:

To correct the error, those two picture areas are used which are on the sides of the reticle opposed to each other and distant from each other. In the shown embodiment, one of those picture areas is selected from the area 203 at the left-hand side and the other is selected from the area 204 at the right-hand side in FIG. 19a.

Taking an imaginary x-y coordinates on the reticle 1, it is obvious that all the small divided individual picture areas are on a matrix arranged according to the x-y coordinates. The thing necessary is to make the x-axis and y-axis of the coordinates coincident with the two-dimensional moving directions of the stage 14. To this end, the operator searches for such a pattern in one picture area j in the area 203 which has a particular edge parallel to the x-axis (which edge is referred to as first horizontal edge), through ITV. At the time, also the coordinate value on y-axis of the edge has to preliminarily obtain from the design data. When the first horizontal edge has been found out, the one picture area j is reproduced on the television screen in the same manner as above. The thing next to be done is to find out such a pattern on design which has a second horizontal edge of the same y-coordinate value as the first horizontal edge found in the one picture area j. The pattern on design having the second horizontal edge is serched for in the design data corresponding to one picture area m in the above-mentioned area 204 opposite to the picture area j. This operation is carried out by the computer 10. If the pattern on design has been found out, then the stage 14 is moved parallel to the x-axis of the coordinate. Thereafter, the one picture area m is image picked up by ITV and the image is reproduced on the television screen. Observing the screen of the monitor television, the operator brings the first and second horizontal edges into a correctly overlapped relation. For this overlapping, the operator finely rotates the reticle 1 relative to the stage 14 by use of a fine rotation mechanism provided at the stage 14 (not shown). It is recommendable that the rotation center be selected at a point near the area 203 of the reticle 1.

In the above alignment operation, if the second horizontal edge is absent in the picture area m, the above procedure is repeated starting from the step of finding out the first horizontal edge in the next one picture area k in the area 203.

As described above, for setting the origin of the coordinate it is required to select one picture area bearing a pattern among nine areas a to i. However, this selection can be done very easily by making an examination of the characteristic information on design of the respective picture areas already prepared during the time of non-defect examination by use of the computer 10.

In the above shown embodiment, the alignment of reticle with stage has been carried out manually while reproducing the necessary images on a monitor television screen. However, the above alignment operations can be carried out also automatically. An arrangement for this automatic alignment is shown in FIG. 20.

Figure 20:
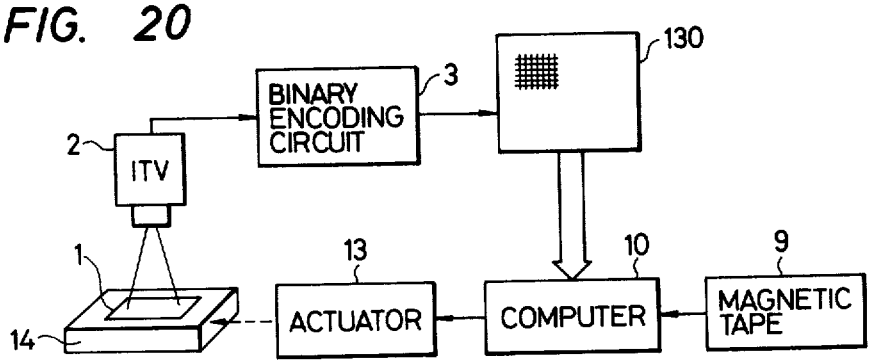
FIG. 20 is a block diagram showing an embodiment of the apparatus for alignment of the examined object.

Referring to FIG. 20, a binary image of a pattern on the reticle 1 is obtained by ITV 2 and the binary encoding circuit 3. The binary image is developed into the above-described frame memory 130 and then the binary information is transferred to the computer 10. The computer 10 makes a comparison between the binary image in the memory 130 and the binary image on design of the pattern based on the design data from the magnetic tape 9. From the result of the comparison, the computer 10 computes the direction and magnitude of the existing deviation thereof. According to the result of the computing, the computer controls the actuator 13 so as to move the stage 14 for alignment.

More concretely, the above automatic alignment is performed in the following manner:

Design data of patterns which are to be present in the picture areas, a to i, j to l and m to o shown in FIG. 19a are previously registered in the memory within the computer 10. The design data include the information of five parameters of rectangular pattern shown in FIG. 4.

For example, at the time of setting the origin, the stage 14 is moved for a rough positioning and one of the picture areas a–i is selected to be image-picked up by ITV 2. For example, ITV 2 picks up the image of area i as one picture. The image is then transformed into a binary image by the binary encoding circuit 3. The pattern information of the binary image is developed into the frame memory. The computer reads in the bit pattern in the frame memory 130 as binary information.

From the design data corresponding to the area i, the computer calculates the positions on design of horizontal and vertical edges of a certain pattern on one hand. On the hand, from the binary information from the frame memory 130 it calculates the positions of horizontal and vertical edges of the corresponding pattern. Thus, the difference in position between the two edges is obtained by computing thereby detecting the existing two-dimensional deviation of the binary image in the frame memory 130 relative to the pattern image on design based on the design data. According to the detected magnitude of deviation, the computer controls the actuator 13 for alignment. The setting of the origin by controlling the actuator 13 in this manner may be carried out before the start of an actual examination for pattern defect, that is, at the time when a reticle or mask is placed on the stage 14. However, it is also possible to make the computer 10 memorize the calculated magnitude of deviation in it as origin offset value. When the stage 14 is moved for carrying out an examination of defect, the computer controls the actuator 13 to move the stage in such manner as to compensate the origin offset value. Thus, the alignment is carried out during the actual examination.

Similarly, the correction of rotational error may be made during the actual examination. The fine rotation mechanism mentioned above may be used for a rough correction of the rotational deviation (inclination). The fine correction of the rotational error is made by the computer 10 which controls the movement of the stage 14. In this case, the above-mentioned areas on the opposed sides (right and left) of a reticle or mask are previously image-picked up by ITV 2. The computer 10 reads in the images through the frame memory 130. The first horizontal edge existing on one side and the second horizontal edge on the opposite side are compared in the computer to compute the existing deviation in y-direction between the two edges. The computer 10 keeps the result of the computing in memory as rotational offset value.

In this manner, the computer 10 has not only the origin offset value but also the rotational offset value stored therein. At the actual examination, the computer 10 drives the stage 14 while compensating the origin offset value and the rotational offset value. Arithmetic operations necessary for the corrections are executed by the computer 10. For origin setting, the computer 10 makes an addition to or subtraction from the coordinate value of the stage 14 according to the origin offset value. For fine correction of rotational error, the computer carries out an arithmetic operation for coordinates transformation based on the rotational offset value so that the two-dimensional movement of the stage 14 can be performed correctly in accordance of the system of rectangular coordinates in the reticle or mask. According to the result of the arithmetic operation, the computer 10 controls the actuator 13.

Figure 21:
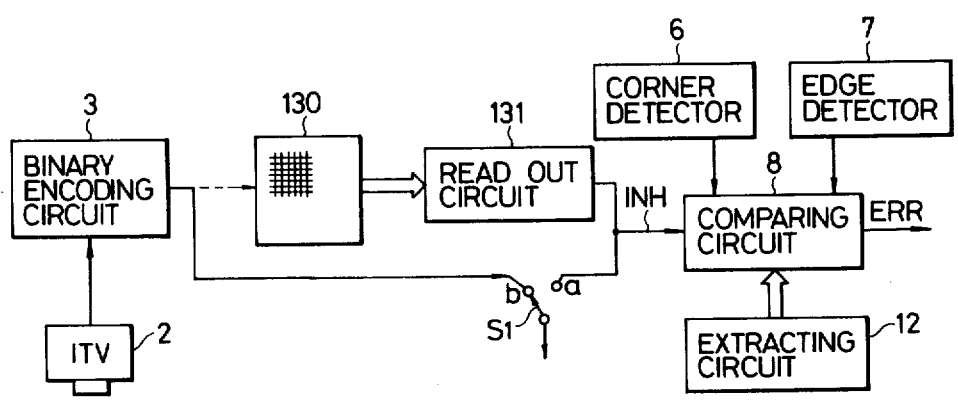
FIG. 21 is a block diagram showing another embodiment of the invention which has accommodation for the presence of damage on the photo-reception surface.

As previously described with reference to FIG. 12, in the above embodiments, the frame memory 130 and the read out circuit 131 are not in operation during the actual examination. However, they may be used to inhibit the operation of the comparing circuit 8 when the photo-reception surface of ITV 2 is damaged, for example, by dust or scratch during the actual examination. FIG. 21 shows an embodiment suitable for this purpose.

In FIG. 21, the switch S1 is in the position connected to the terminal b for actual examination.

Prior to the start of an actual examination by comparison as described above, ITV 2 scans a blank image containing no pattern, that is, an image of the photo-reception surface containing only damage or damages, if any. The output binary image signal obtained the scanning is introduced into the frame memory 130 which forms a binary image corresponding to the damage. If there is any damage on the photo-reception surface, therefore, the frame memory 130 has an input, for example, logic "1" at the corresponding bit. Where there is no damage logic "0" is put in. After completing this preoperation, ITV 2 starts scanning of the original image of the pattern to be actually examined. In synchronism with the scanning, the read out circuit 131 reads out from the frame memory 130 in time series the logical value of the bit corresponding to the picture element now being scanned. This time-series binary signal is introduced into the comparing circuit 8 as inhibit signal INH. The comparing circuit 8 carries out a comparison in the manner as described above. However, when the inhibit signal INH is logic "1", the comparing operation is inhibited by it or the output of defect information ERR from the comparator 8 is inhibited by it although it allows the comparator to continue comparing.

The use of the frame memory 130 according to this embodiment enables to prevent any error of examination due to the damage on the photo-reception surface in real time. Such a damage on the photo-reception surface has been often misjudged by the detector as the presence of defect in the examined pattern. According to above embodiment, such misjudgement can be eliminated. According to the embodiment, it is also possible to set a comparison inhibiting area for any desirable area in one picture to be examined. This may be realized by suitably managing the binary image in the frame memory 130.

In forming the binary image of the damage on the photo-reception surface in the frame memory 130 according to the above embodiment, it is not necessary to pick up the blank image by ITV 2 and form the binary image thereof every time of examination of one picture. The reason for this is that the position of the damage on the photo-reception surface does not change in a short time. Therefore, data of the binary image of such damage may be stored in the computer 10. When necessity arises, the data may be again transferred to the frame memory 130. Since dust on the photo-reception surface increases with time, the data have to be renewed at suitable time intervals.

While the invention has been particularly shown and described with reference to preferred embodiments thereof. It will be understood that many modifications and variations are possible in the light of the above teachings. The objects which can be examined are never limited to reticles and masks for use in the manufacture of semiconductor integrated circuits only. The present invention is also applicable to the examination of masks for use in the manufacture of printed substrates. In this case, if the pattern of the mask for print substrate has been designed depending on a pattern making data according to CAD (Computer Aided Design), the data necessary for the apparatus of the invention as design information may be provided by a format conversion of the pattern making data.

Also, instead of image scanning by image-pickup apparatus such as ITV as shown in the above embodiments, there may be used direct scanning by laser spot or the like. In this case, the pattern on reticle or mask is scanned directly by the spot of laser beam and the image signal is produced by detecting the reflected or transmitted light which varies according to the pattern. By doing so, the apparatus according to the invention can be used also to examine relief patterns.

In the above embodiments, the corner of a pattern has been detected as the characteristics of the pattern. However, the present invention may be carried out also by detecting other characteristics relating to shape of the examined pattern such as triangle, square and annular shape. Further, the present invention may be carried out by detecting the characteristics relating to the change of edge appearing on the scanning line during the pattern scanning such as the number of edges, the number of picture elements between one edge and the next edge.

We claim:

1. Apparatus for examining a pattern consisting of bright parts and dark parts formed on an examined object based upon design data, said apparatus comprising:
    scanning means for scanning said pattern and producing binary signals according to the pattern;
    first extracting means for serially extracting binary information corresponding to a determined area on said examined object from said binary signals;
    first detection means for detecting a geometrical shape of the pattern in said determined area based on said binary information;
    second detection means for detecting the edge portion between the bright part and the dark part of the pattern in said determined area;
    second extracting means for extracting from said design data information relating to the geometrical shape which said pattern should have; and
    examination means for producing defect information indicative of the presence or absence of any defect in the pattern in said determined area in response to said second detection means when the information extracted by said second extracting means and the information detected by said first detection means agree with each other.

2. Apparatus for examining a pattern on an examined object through the steps of scanning a geometric pattern formed on said object to obtain image signals corresponding to the pattern, detecting a geometrical shape of the pattern in a determined area on said object based on the image signals to produce detection information, and comparing said detection information with design data, said apparatus having improvements comprising:
    means for forming said detection information, said means being adapted to detect a determined corner from the pattern in said determined area; and
    encoding means for encoding said detected corner in such manner that one of two corners having the same angle and being point-symmetric to each other is given a first code and the other corner is given a second code.

3. In an apparatus for examining a pattern formed on an examined object having means for scanning said pattern to produce image binary information for transforming the image of said pattern into picture elements and means for producing design binary information for forming a binary image of the design of said pattern based on design data and wherein the characteristics of said pattern and the characteristics of said design that said pattern should possess are compared with each other based on said image binary information and said design binary information, the improvements comprising:
    means for detecting, based on said design binary information, said characteristics of the design of said pattern which should appear on a scanning line of said scanning means and giving a determined binary code to the detected characteristics; and
    memory means adapted to keep said binary code in memory every time the image of the pattern is transformed into a predetermined number of picture elements by said scanning means.

4. Apparatus for examining a geometrical pattern formed on an examined object comprising:
    scanning means for scanning the original image of said pattern to produce image binary information of the picture elements of said original image;
    memory means having memory units each corresponding to each picture element of said original image and able to store binary information in every memory unit, said memory means being capable of developing said stored binary images;
    means for forming a design binary image which said original should have on design based on said design data;
    means for forming an inhibition binary image for setting an examination inhibition area in said original image;
    control means for selectively developing said design binary image and said inhibition binary image;
    accumulation means for detecting predetermined characteristics of said pattern to be examined from said design binary image of said memory and accumulating the detected information; and
    examination means for examining the defect of said pattern based on said image binary information and above detected information by said accumulation means and inhibiting said examination with reference to the inhibition binary image of said memory means.

5. Apparatus for examining a geometric pattern formed on an examined object said apparatus comprising:
    scanning means for scanning the pattern in a determined area on said object to produce an image binary signal for converting the image of said pattern into picture elements;
    image memory means provided with memory bits corresponding to the individual picture elements of said pattern image and for memorizing a bit pattern corresponding to said pattern image depending on the input of said image binary signal;

means for providing design data corresponding to the geometric pattern in said determined area;

moving means for moving said scanning means and said examined object relative to each other to set said determined area at any optional positon on said object; and means for computing from said design data the position of the pattern which should be within said determined area, thereby detecting the deviation of said pattern position from the position of said bit pattern in said image memory means, and for controlling said moving means according to the deviation in such manner as to reduce the magnitude of the deviation to a value under a determined value.

6. Apparatus according to claim 1, wherein said first detection means includes means which detects a substantially corner shape from the pattern of said determined area.

7. Apparatus according to claim 2, wherein said forming means includes means detecting a corner having an angle of about 90 degrees and means detecting a corner having an angle of about 135 degrees.

8. Apparatus for examining a pattern on an examined object through the steps of scanning a geometric pattern formed on said object to obtain image signals corresponding to the pattern, detecting a geometrical shape of the pattern in a determined area on said object based on the image signals to produce detection information and comparing said detection information with design data, said apparatus having improvements comprising:

means for forming said detection information, said means being adapted to detect a determined corner from the pattern in said determined area; and means which encodes said detected corner so that different binary codes may be provided between corners having different angles.

9. Apparatus according to claim 8, wherein said pattern consists of relatively bright parts and dark parts and wherein said encoding means provides the same binary codes if a corner formed by a portion of said bright parts and a corner formed by a portion of said dark parts are formed at the same position and at corresponding angles with respect to said determined area.

10. Apparatus according to claim 3, wherein said scanning means scans along plural scanning lines to cover a determined area of said pattern and said memory means includes at least one register means having a number of memory bits equal to the number of picture elements corresponding to one of said plural scanning lines divided by said predetermined number.

* * * * *